(12) United States Patent
Lang et al.

(10) Patent No.: US 8,303,578 B2
(45) Date of Patent: Nov. 6, 2012

(54) SYSTEM AND METHOD FOR THE TREATMENT OF A PATIENTS EYE WORKING AT HIGH SPEED

(75) Inventors: Stefan Lang, Markt Schwaben (DE); Roland Toennies, Olching (DE)

(73) Assignee: Technolas Perfect Vision GmbH, Munich (DE)

( * ) Notice: Subject to any disclaimer, the term of this patent is extended or adjusted under 35 U.S.C. 154(b) by 1259 days.

(21) Appl. No.: 12/063,900

(22) PCT Filed: Sep. 27, 2006

(86) PCT No.: PCT/EP2006/009394
§ 371 (c)(1),
(2), (4) Date: Feb. 15, 2008

(87) PCT Pub. No.: WO2007/039207
PCT Pub. Date: Apr. 12, 2007

(65) Prior Publication Data
US 2008/0234667 A1    Sep. 25, 2008

(30) Foreign Application Priority Data
Sep. 27, 2005 (DE) .......................... 10 2005 046 130

(51) Int. Cl.
*A61B 18/18* (2006.01)
(52) U.S. Cl. .............................. 606/5; 604/294; 351/208
(58) Field of Classification Search .................. 606/3–6, 606/10–12, 16–19, 42, 166, 167; 351/211, 351/212, 214–217, 233, 205
See application file for complete search history.

(56) References Cited

U.S. PATENT DOCUMENTS
4,715,703 A    12/1987 Cornsweet et al.
(Continued)

FOREIGN PATENT DOCUMENTS
DE    19727573    5/1998
(Continued)

OTHER PUBLICATIONS
International Search Report regarding U.S. Appl. No. 12/063,900; International Application No. PCT/EP2006/009394; Date of Completion: Dec. 14, 2006; Date of Mailing: Dec. 20, 2006.
(Continued)

*Primary Examiner* — Melanie Hand
(74) *Attorney, Agent, or Firm* — Akin Gump LLP; David R. Clonts

(57) ABSTRACT

The invention relates to a system and a method for the treatment of a patient's eye. The system comprises a laser apparatus, a scanning apparatus and an eye tracking apparatus for determining the actual position of the patient's eye and for generating alignment data of the patient's eye relative to a reference position of the patient's eye to the laser, said eye tracking apparatus being provided with a desired treatment shot file. Said scanning apparatus is connected via a first bidirectional bus to the eye tracking apparatus, said laser apparatus is connected via a second bidirectional bus to the eye tracking apparatus. The eye tracking apparatus adjusts the position data for each shot based on said alignment data of the patient's eye and provides aiming control signals representative of the target position data to the scanning apparatus for said shot via said first bidirectional bus. The eye tracking apparatus comprises a comparator for comparing the target position data with the actual position data provided by the scanning apparatus for the shot to be fired. Moreover, said eye tracking apparatus is sending a command signal to the laser apparatus via said second bidirectional bus for firing the shot when the target position data is equal to the actual position data of the scanning apparatus for the shot to be fired.

36 Claims, 5 Drawing Sheets

U.S. PATENT DOCUMENTS

| | | |
|---|---|---|
| 4,848,340 A | 7/1989 | Bille et al. |
| 5,098,426 A | 3/1992 | Sklar et al. |
| 5,347,331 A | 9/1994 | Isogai et al. |
| 5,360,424 A | 11/1994 | Klopotek |
| 5,430,507 A | 7/1995 | Nishio et al. |
| 5,526,072 A | 6/1996 | El Hage |
| 5,549,632 A | 8/1996 | Lai |
| 5,620,436 A | 4/1997 | Lang et al. |
| 5,624,436 A | 4/1997 | Nakamura et al. |
| 5,644,375 A | 7/1997 | Suzuki |
| 5,752,950 A | 5/1998 | Frey et al. |
| 5,772,656 A | 6/1998 | Klopotek |
| 5,865,832 A | 2/1999 | Knopp et al. |
| 5,889,577 A | 3/1999 | Kohayakawa |
| 5,947,955 A | 9/1999 | Kadambi et al. |
| 5,949,521 A | 9/1999 | Williams |
| 6,033,075 A | 3/2000 | Fujieda |
| 6,082,860 A | 7/2000 | Takagi |
| 6,086,204 A | 7/2000 | Magnante |
| 6,095,651 A | 8/2000 | Williams |
| 6,099,522 A | 8/2000 | Knopp et al. |
| 6,149,643 A * | 11/2000 | Herekar et al. .......... 606/5 |
| 6,159,202 A | 12/2000 | Sumiya et al. |
| 6,195,164 B1 | 2/2001 | Thompson et al. |
| 6,210,401 B1 | 4/2001 | Lai |
| 6,283,954 B1 | 9/2001 | Yee |
| 6,302,879 B1 | 10/2001 | Frey et al. |
| 6,322,216 B1 | 11/2001 | Yee et al. |
| 6,361,168 B1 | 3/2002 | Fujieda |
| 6,394,999 B1 | 5/2002 | Williams |
| 6,409,343 B1 | 6/2002 | Uchida |
| 6,409,345 B1 | 6/2002 | Molebny |
| 6,413,251 B1 | 7/2002 | Williams |
| 6,439,719 B2 | 8/2002 | Hayashi et al. |
| 6,451,008 B1 | 9/2002 | Frey et al. |
| 6,488,676 B1 | 12/2002 | Glockler et al. |
| 6,491,687 B1 | 12/2002 | Sumiya et al. |
| 6,494,577 B2 | 12/2002 | Iwanaga |
| 6,500,171 B1 | 12/2002 | Williams |
| 6,508,812 B1 | 1/2003 | Williams |
| 6,579,282 B2 | 6/2003 | Bille et al. |
| 6,585,724 B2 | 7/2003 | Toh |
| 6,588,902 B2 | 7/2003 | Isogai |
| 6,607,527 B1 | 8/2003 | Ruiz et al. |
| 6,610,049 B2 | 8/2003 | Lai et al. |
| 6,626,894 B2 | 9/2003 | Frey et al. |
| 6,626,895 B2 | 9/2003 | Frey et al. |
| 6,626,896 B2 | 9/2003 | Frey et al. |
| 6,666,857 B2 | 12/2003 | Smith et al. |
| 6,669,340 B2 | 12/2003 | Percival et al. |
| 6,706,036 B2 | 3/2004 | Lai |
| 6,712,809 B2 | 3/2004 | Li et al. |
| 6,715,877 B2 | 4/2004 | Molebny |
| 6,733,129 B2 | 5/2004 | Masaki |
| 6,749,302 B2 | 6/2004 | Percival et al. |
| 6,786,899 B1 | 9/2004 | Lai |
| 6,848,790 B1 | 2/2005 | Dick |
| 6,923,802 B2 | 8/2005 | Williams |
| 6,932,475 B2 | 8/2005 | Molebny |
| 6,945,650 B2 | 9/2005 | Beverly |
| 6,997,555 B2 | 2/2006 | Dick |
| 7,044,602 B2 | 5/2006 | Chernyak |
| 7,237,895 B2 | 7/2007 | Ogawa |
| 7,258,443 B2 | 8/2007 | Masaki |
| 7,258,686 B2 | 8/2007 | Maeda et al. |
| 7,380,942 B2 | 6/2008 | Molebny |
| 7,390,089 B2 | 6/2008 | Loesel et al. |
| 7,682,023 B2 | 3/2010 | Van Saarloos |
| 7,721,743 B2 | 5/2010 | Lenzner et al. |
| 7,842,030 B2 | 11/2010 | Muhlhoff |
| 2002/0013573 A1 | 1/2002 | Telfair et al. |
| 2002/0082590 A1 | 6/2002 | Potgieter |
| 2005/0159733 A1 | 7/2005 | Dick |
| 2008/0234667 A1 | 9/2008 | Lang et al. |
| 2009/0093798 A1 | 4/2009 | Charles |
| 2009/0182310 A1 | 7/2009 | Gertner et al. |
| 2009/0182312 A1 | 7/2009 | Gertner et al. |
| 2009/0299347 A1 | 12/2009 | Vogler et al. |
| 2011/0118712 A1 | 5/2011 | Lubatschowski et al. |

FOREIGN PATENT DOCUMENTS

| | | |
|---|---|---|
| DE | 20 2005 018911 | 3/2006 |
| DE | 10 2005 006897 | 8/2006 |
| EP | 0697611 | 2/1996 |
| EP | 1396244 A2 | 3/2004 |
| EP | 1719483 | 11/2006 |
| EP | 1402860 B1 | 5/2007 |
| JP | 2000300596 | 10/2000 |
| JP | 2002524144 | 8/2002 |
| WO | 9424968 | 11/1994 |
| WO | 9527535 | 10/1995 |
| WO | 9611655 | 4/1996 |
| WO | 9848746 | 11/1998 |
| WO | 0124688 | 4/2001 |
| WO | 0128410 A | 4/2001 |
| WO | 0128477 A1 | 4/2001 |
| WO | WO01/28476 | 4/2001 |
| WO | 0234178 | 5/2002 |
| WO | 03068103 | 8/2003 |
| WO | 03075778 | 9/2003 |
| WO | 2004041104 | 5/2004 |
| WO | 2004052253 A1 | 6/2004 |
| WO | 2004053568 | 6/2004 |
| WO | 2004095187 | 11/2004 |
| WO | 2005007002 | 1/2005 |
| WO | WO95/27453 | 10/2005 |
| WO | 2007012924 | 2/2007 |
| WO | 2007143111 | 12/2007 |

OTHER PUBLICATIONS

Damien Gatinel, et al., "Three-dimensional representation and qualitative comparisons of the amount of tissue ablation to treat mixed and compound astigmatism," Journal of Cataract and Refractive Surgery, vol. 28 (No. 11) p. 2026-2034 (Nov. 1, 2002).

* cited by examiner

SYSTEM AND METHOD FOR THE TREATMENT OF A PATIENTS EYE WORKING AT HIGH SPEED

FIELD OF THE INVENTION

The present invention relates to a system and a method for the treatment of the patient's eye with high speed, in particular to a system and a method using a refractive laser system.

DESCRIPTION OF THE RELATED ART

WO 95/27453 A relates to an excimer laser eye surgery system using an optical aiming system which is schematically shown in FIG. 1. The excimer laser eye surgery system 10 is used for a non-invasive resculpting of the surface of the eye 44 by providing shots from an excimer laser 20 at desired locations on a determined treatment area of an eye. With a typical excimer laser, a pulsed beam 22 is provided with typical repetition rates of 60 to 100 pulses per second with a typical pulse length of 10 to 30 ns and having a pulse energy of about 200 mJ/pulse. An aiming laser 32 provides an aiming beam spot which coincides with the central axis of the laser shot of the pulsed beam. A registration laser 35 provides a registration beam which is coaxially aligned with the pulsed beam. The pulsed beam coaligned with the aiming beam from the aiming laser 32 and the registration beam from the registration laser 35 passes from optics through an adjustable diaphragm 36 which allows the beam size of the pulsed beam to be adjusted before it enters the final optics. Following the adjustable diaphragm 36, a focussing lens 40 directs the pulsed beam onto a scanning mirror 42, which then reflects the beam onto a patient's eye 44. The scanning mirror is capable of moving a beam at 5000 mm/s at the surface of the eye. The focussing lens 40 focuses light such that when the eye is at the optimal distance, the pulsed beam is properly focussed onto the eye. Also provided in the system is a focussing laser 46 whose beam travels through optics and impinges on the eye 44 at an angle. The distance of the eye from the eye surgery system is adjusted such that both the beam from the aiming laser 32 and the beam from the focussing laser 46 impinge on the surface of the eye at the same point. This known system comprises a control unit 64 which controls all components of the eye surgery system 10 including the diaphragm 36, the scanning mirror 42 and shutters 28, 33 and 48 for blocking transmission of the pulsed beam, the aiming beam and the focussing beam. A microscope 56 is provided for the physician to observe progress during ablation of the surface of the eye, wherein the microscope focuses through the scanning mirror 42 and a splitting mirror 58. The splitting mirror 58 provides a view of the eye 44 to a video camera 60. The control unit 64 further contains an eye tracking system 70. The video camera 60 provides an image output to the control unit 64 and a capturing video screen 62. An ablation profile software running in the control unit 64 calculates the coordinates relative to the origin of a desired target point, which denotes the centre of the next desired excimer pulse on the eye 44 from the excimer laser 20. Having received the absolute coordinates of where the origin is located on the video image from the eye tracking system 70, the ablation profile software then knows the absolute coordinates of the target point. Then, the image from a video camera 60 allows the eye tracking system 70 to locate and provide the absolute coordinates of a registration spot where the registration beam from the registration laser impinges on the eye. This registration spot denotes the centre point of where the next pulse from the excimer laser would impinge on the eye if the shot were immediately fired. In case this point is not in alignment with the desired target point because of any intervening movement of the eye, the aim of the pulsed beam is therefore corrected such that the registration spot coincides with the target point. This alignment is then again checked and when within acceptable limits, the excimer laser 20 is fired.

An advantage of this technique is the fact that the registration beam from the registration laser is aligned with the pulsed beam from the pulsed excimer laser 20. If the movable mirror 42 is uncalibrated, this does not matter, because one always knows where the next shot from the excimer laser will actually fall. Further, misalignment of the video camera 60 along the optical axis is similarly of no consequence, as the control unit using the video camera can always determine where the next shot from the pulsed excimer laser will strike relative to the origin. Further, slight misalignment of the registration laser 35 is similarly of no consequence as that misalignment will result in a fixed offset from the centre of the pulsed beam. Simple calibration software can determine this offset, and then corrects for this offset in determining where the centre of the next shot from the excimer laser 20 will fall relative to the registration spot. Using a specific software routine in conjunction with the registration laser 35 and the eye tracking system 70, the ablation profile software can accurately position the pulsed beam for the firing of the next shot.

WO 01/028476 A1 relates to a system and method using iris recognition for adjustment during diagnosis and during surgery. Based on data provided by a diagnostic tool, a treatment is developed. This treatment is normalised to the spot representation of the iris image. The treatment itself is aligned to the iris of the patient. Normalisation can take very general forms, such as a translation of the aim of the laser to an appropriate point, or more sophisticated forms, such as by rotation or even scaling and skewing of the treatment to match the iris image that is presented to the laser system. The laser treatment is then performed. During the laser treatment, the system can periodically or even continuously match the iris data to the stored representation of the iris data, in essence tracking the patient's eye. It is possible for each shot to be appropriately rotated and translated. The iris image can be tracked and the scaling functions applied dynamically to each specific shot or sequence of shots in the desired treatment pattern. In this manner, the movement of the eye can be accommodated shot-by-shot.

U.S. Pat. No. 5,624,436 relates to an apparatus for ablating an object by laser beam having means to correct the refractive power of the laser beam. In order to control the ablating operation, in particular the ablating depth per pulse, it is suggested to use a reference plate which is disposed at a position where usually the cornea of the eye is to be disposed. After performing an ablation operation, the resulting ablation depth is determined. As a reference plate, a transparent plate made from polymethylmethacrylate resin (PMMA) may be used and the refractive power of the simulated lens produced on the transparent plate can be measured and compared with the refractive power of a lens to be formed at the referenced ablation rate. Where the reference plate is made of non-transparent material, a reflection focal length by collimator can be measured.

U.S. Pat. No. 5,772,656 relates to a calibration apparatus for measuring the properties of a laser beam. The calibration apparatus includes a photo reactive element which is formed from a erodable material having ablation characteristics similar to that of biological tissue, for example polymeric coating of polymethylmethacrylate (PMMA), polymethylstyrene, polycarbonate or mixtures thereof, and as an example polycarbonate calibration records fabricated from LEXAN® resins (commercially available from General Electrical, Pitsfield, Mass. or from CR-39® resins (PPG Industries, Pittsburgh, Pa.). After performing a reference treatment of the photoreactive element, the resulting change following exposure to the ablative laser radiation is detected by inspection of the change of the optical properties. The records can be analysed to generate or feedback signals.

U.S. Pat. No. 6,195,164 B1 relates to systems and methods for calibrating laser ablation. The optical power and shape of a test surface that has been ablated by energy delivered from a laser is measured. The known optical properties of the ablated test surface may be used to adjust the laser ablation system by varying treatment parameters such as laser pulse intensity and exposure time.

SUMMARY OF THE INVENTION

The object underlying the present invention is to provide a system and a method for the treatment of a patient's eye working at high speed.

This object is solved with the features of the claims.

The present system and method is particularly suitable for treatment with a laser working at a high pulse rate of for example 200 Hz, preferably 500 Hz and more preferably 1000 Hz or more.

In the system according to the present invention, the eye tracking apparatus which determines the actual position of the patient's eye and which generates alignment data of a patient's eye relative to a reference position of the patient's eye is provided with a desired treatment shot file. The eye tracking apparatus adjusts the position data for each shot to be fired based on said alignment data of the patient's eye and provides aiming control signals representative of the target position data to the scanning apparatus for said shot. The eye tracking apparatus comprises a comparator for comparing the target position data with actual position data provided by the scanning apparatus for the shot to be fired and as soon as the target position data is equal to the actual position of the scanning apparatus for the shot to be fired, a command signal is sent to the laser for firing the shot. In the system according to the present invention, the eye tracking apparatus, and the scanning apparatus are connected via a first bidirectional bus and the eye tracking apparatus and the laser are connected via a second bidirectional bus. The first bidirectional bus preferably comprises a wire connection. The second bidirectional bus preferably comprises an optical fibre connection. This has the advantage that the optical data transmission is not disturbed by any electromagnetic field.

The system of the present invention has the advantage that the eye tracking apparatus is provided with the desired treatment shot file and performs control over the scanning apparatus and the laser apparatus. Compared to known systems, the system according to the present invention provides faster control of the scanning apparatus and the laser apparatus.

According to a preferred embodiment of the present system, the laser apparatus sends a feedback signal to the eye tracking apparatus via said second bidirectional bus as soon as a shot has been fired. If the eye tracking apparatus receives this feedback signal within a predetermined time, the eye tracking apparatus processes to the next shot otherwise the eye tracking apparatus stops further processing of the treatment shot file. The predetermined time t amounts to 1 ms to 100 ms. The minimum amount is selected corresponding to the pulse rate of the laser.

According to a further embodiment of the invention, the scanning apparatus comprises at least one movable mirror and detector means for providing detection signals representative of the actual position of the movable mirror for the shot to be fired to the patient's eye. Alternatively or additionally, the aiming means comprises an aiming laser for providing an aiming beam to the actual position of a shot to be fired on the patient's eye and wherein the eye tracking apparatus determines the actual position of the aiming beam on the patient's eye.

According to an improvement of the invention, the eye tracking apparatus comprises protocolling means for storing protocol information with respect to the operation of the eye tracking apparatus, the scanning apparatus and/or the laser apparatus for every shot. The protocol information preferably comprises at least one of the actual position data of the patient's eye, the actual position data of the scanning apparatus, target position data and any malfunction data.

According to another aspect of the present invention, the system comprises a computer system being connected to the eye tracking apparatus via a third bidirectional bus wherein the computer system provides the desired treatment shot file to the eye tracking system and/or receives and stores protocol information from the eye tracking apparatus, and/or transmits and receives control data to and from the laser apparatus for every shot. Said protocol information may be stored in the computer system alone or additionally in the eye tracking apparatus. The protocol information may be used for any later quality control or for completing an interrupted treatment.

The first, second and third bidirectional busses are independent from each other. This has the advantage that high speed data communication can be performed on each respective bus.

In the system, the third bidirectional bus is used for fast transfer of data between the individual components. This third bidirectional bus is preferably a CAN-bus. Each of the eye tracking apparatus, the laser and the computer comprises a CAN-bus controller. Any other bidirectional bus system according to industrial standard for fast transfer of data may be used.

According to a further aspect of the present invention, the scanning apparatus comprises two moveable mirrors and one fixed mirror wherein the two moveable mirrors are smaller in size than the fixed mirror. The two moveable mirrors are positioned according to the aiming control signals, each one of the two mirrors being moveable by a respective actuator and the actual position of each mirror being detected by a respective position sensor. This has the advantage that compared to known systems using one larger movable mirror the aiming of the laser can be performed at higher speed with two movable mirrors which are smaller and lighter. At the same time, the fixed mirror may be larger than the two movable mirrors and can be used as a half-mirror at a position above the patient's eye so that other optical means like a microscope can be used.

According to a further improvement of the invention, the system comprises further monitoring means for monitoring the energy of the laser. The monitoring means preferably comprise an acoustical sensor for detecting the noise which is generated when a laser pulse of the laser hits on a reference surface. The reference surface is preferably a plate made of plastics, preferably PMMA.

The acoustical sensor may comprise a microphone, which provides a voltage signal, when a laser pulse hits on the reference surface. The acoustical sensor further comprises processing means which receives said voltage signal and generates a reference data which is a measure of the laser energy of the laser pulse and correspondingly a measure of the ablation rate. For a more detailed description of this monitoring means reference is made to the co-pending patent application of the present applicant with the title "Apparatus and Method for monitoring the energy of a laser".

The laser apparatus may further comprise energy control means, which receives the reference data and adjusts the energy of the laser in response to the reference data such that the ablation rate is adjusted.

According to a preferred embodiment of the invention, every n-th laser pulse from a series of laser pulses is directed to a defined position on the reference surface, where n is a natural number greater than 2, preferably 25. The corresponding voltage signal of every n-th laser pulse is evaluated. This has the advantage that the processing means for evaluating the voltage signal can be simplified while the laser is tested under normal operating condition, i.e. at a high pulse rate.

The acoustical sensor preferably measures the propagation time of the noise produced at the reference surface which is then used for monitoring the distance between the reference surface and the acoustical sensor. The acoustical sensor is connected to the laser via said second bidirectional bus. This has the advantage that the measurement of the propagation time can be triggered by the command signal which is sent from the eyetracking apparatus to the laser for firing the shot.

BRIEF DESCRIPTION OF THE DRAWINGS

The invention will be further described by way of examples with reference to the drawings, in which.

DETAILED DESCRIPTION OF THE PREFERRED EMBODIMENT

Figure 1:
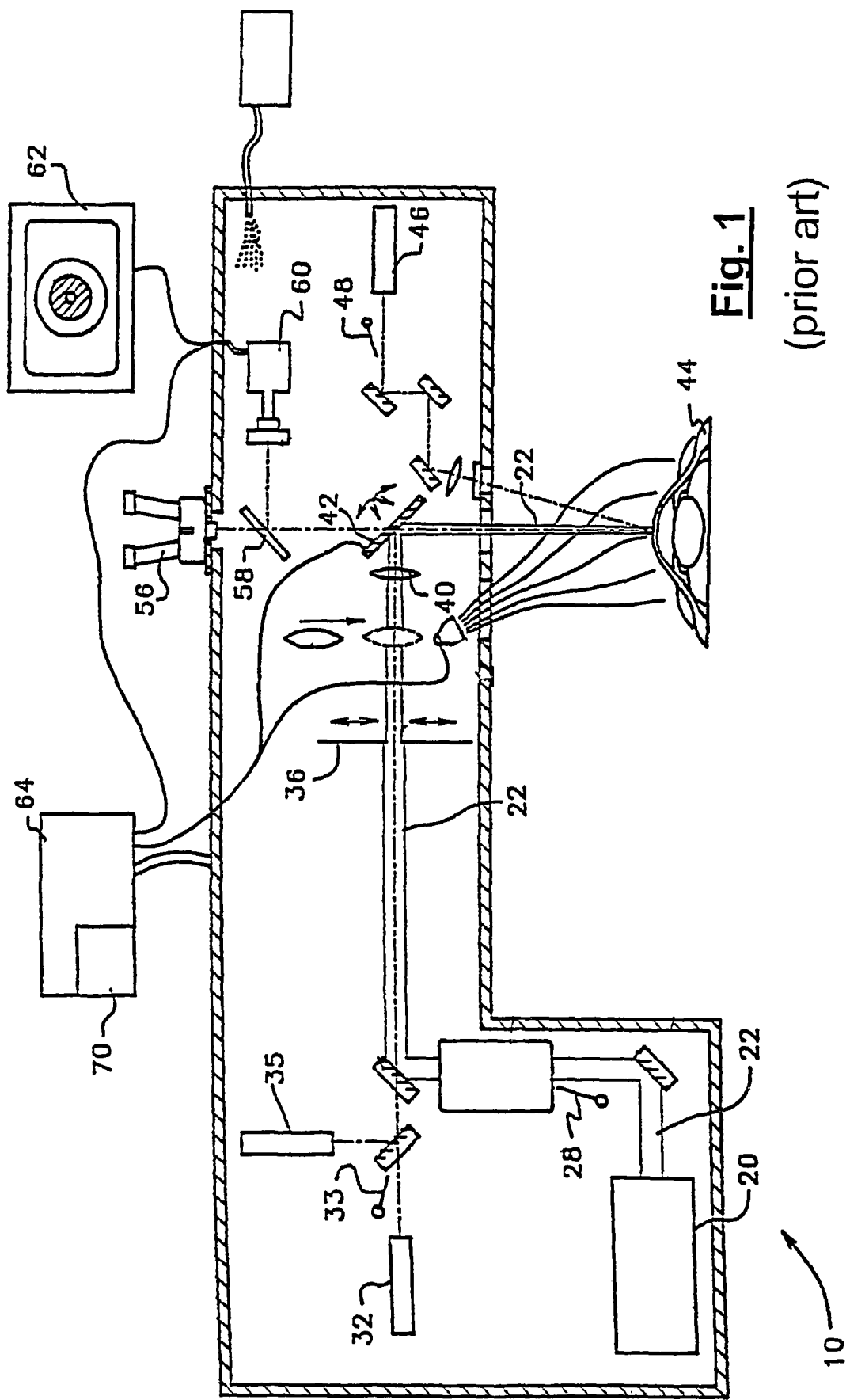
FIG. 1 is a diagram illustrating a known excimer laser eye surgery system.
Figure 2:
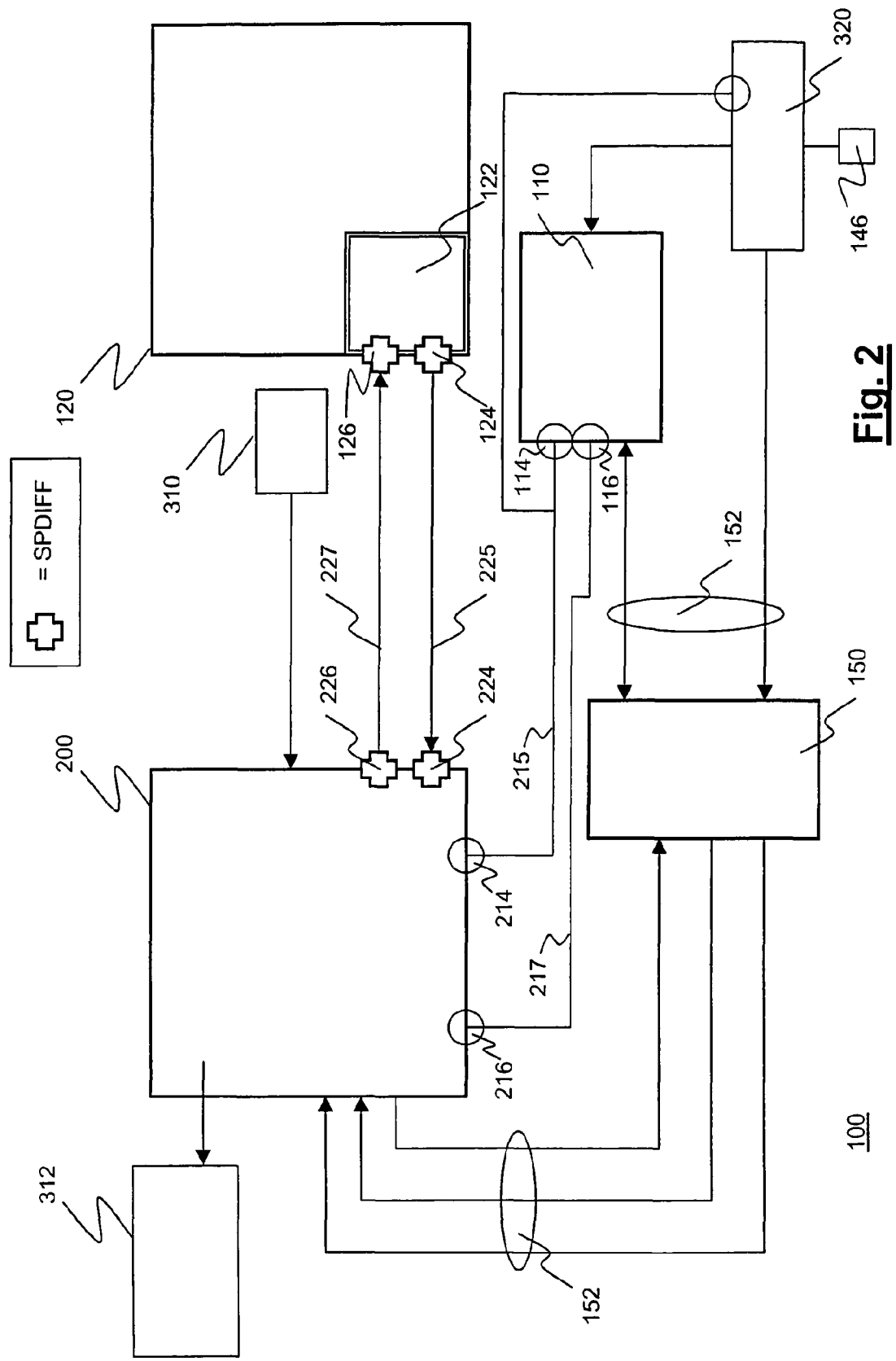
FIG. 2 is a block diagram illustrating the preferred embodiment of an excimer laser eye surgery system according to the present invention.

FIG. 2 shows a block diagram of the preferred embodiment of an eye surgery system 100 according to the present invention. This system comprises in the form of separate modules an excimer laser apparatus 110, a scanning apparatus 120, a personal computer 150 and an eye tracking apparatus 200. The scanning apparatus 120 comprises a scanning control module 122 which is connected to a first interface 124 for receiving data from the eye tracking apparatus and a second interface 126 for transmitting data to the eye tracking apparatus. In the preferred embodiment the interface is realised by a SPDIFF (Siemens Philips data interface). The eye tracking apparatus 200 comprises a first and a second interface, 224 and 226 which are preferably also realised as SPDIFF. The first interface 224 of the eye tracking apparatus is connected to the first interface 124 of the scanning apparatus via a first data communication line 225. The second interface 126 of the scanning apparatus is connected to the second interface 226 of the eye tracking apparatus via a second data communication line 227. The first and second data communication line in combination represent a first bidirectional bus for a fast transfer of digital data between the scanning apparatus and the eye tracking apparatus. In the preferred embodiment the first and second data communication lines are realised as electrical cables. The second data communication line 227 is used for sending position data with regard to the x and y position of the laser beam from the eye tracking apparatus to the scanning apparatus. These position data are used for positioning at least one movable scanning mirror provided in the scanning apparatus. The first data communication line 225 is used for transferring positioning feedback data from the scanning apparatus to the eye tracking apparatus which represent the actual position of the movable mirror in the scanning apparatus. Said positioning feedback data can be for example provided by a detector which is related to a controlling means for positioning the movable mirror.

The excimer laser apparatus 110 comprises a first and a second optical interface 114 and 116, respectively. The eye tracking apparatus further comprises a first and second optical interface 214 and 216, respectively. Said first optical interfaces 114 and 214 are connected via an energy monitoring means 320 by means of first optical cables 215. The energy monitoring means 320 comprises a first and a second optical interface 314a, 314b. The second optical interfaces 116 and 216 are connected by means of a second optical cable 217. Both optical cables 215 and 217 in combination represent a second bidirectional bus. Via the first optical cable 215 a command signal is fed from the eye tracking apparatus through the energy monitoring means to the excimer laser apparatus. Via the second optical cable 217 a feedback signal is fed from the excimer laser apparatus to the eye tracking apparatus. Using optical data communication for the connection between the eye tracking apparatus and the excimer laser apparatus has the advantage that data communication is safe without distortion by noise.

The excimer laser system 100 comprises a third bidirectional bus 152 for connecting the personal computer 150 with the excimer laser apparatus 110 and with the eye tracking apparatus 200. Preferably, the third bidirectional bus is realised as a CAN-bus, wherein each of the personal computer 150, the excimer laser apparatus 110 and the eye tracking apparatus 200 comprises respective CAN-controllers (not shown). The data connection between the personal computer 150 and excimer laser apparatus 110 is used for example for transferring data regarding a status of the excimer laser apparatus, i.e. for determining whether the high voltage is switched on or whether the excimer laser apparatus is in the stand-by mode. FIG. 2 schematically shows an infrared camera 310 which is providing video data to the eye tracking apparatus 200 with respect to an image taken from an eye to be treated with the excimer laser eye surgery system 100. FIG. 2 additionally shows an infrared-light source 312 which is connected to the eye tracking apparatus 200 and preferably illuminates the eye to be treated with a pulsed infrared light.

The excimer laser eye surgery system according to the present invention has the advantage that the individual apparatuses are connected to each other via input/output interfaces which allows for fast and standardised data communication. As will become clear from the further description, the eye tracking apparatus 200 receives the necessary data for providing control over the scanning apparatus on the one hand and the excimer laser apparatus on the other hand. This allows a fast processing of data so that in the system for processing a determined treatment a pulsed beam may be provided with a repetition rate of 1000 pulses per second and more.

The system shown in FIG. 2 further comprises an energy monitoring means 320 for monitoring the pulse energy of the pulses which are applied to a patient's eye. When a command signal is sent from the eye tracking apparatus 200 to the excimer laser apparatus 110 through the energy monitoring means 320 both start operation. The energy monitoring means 320 is further connected to the personal computer 150. Depending on the output of the energy monitoring means the personal computer will provide data to the excimer laser apparatus for adjusting the laser energy by for example changing the high voltage or provide warning signals or a shut down signal to the excimer laser apparatus when the energy of laser is out of the determined range for operating the system.

Figure 3:
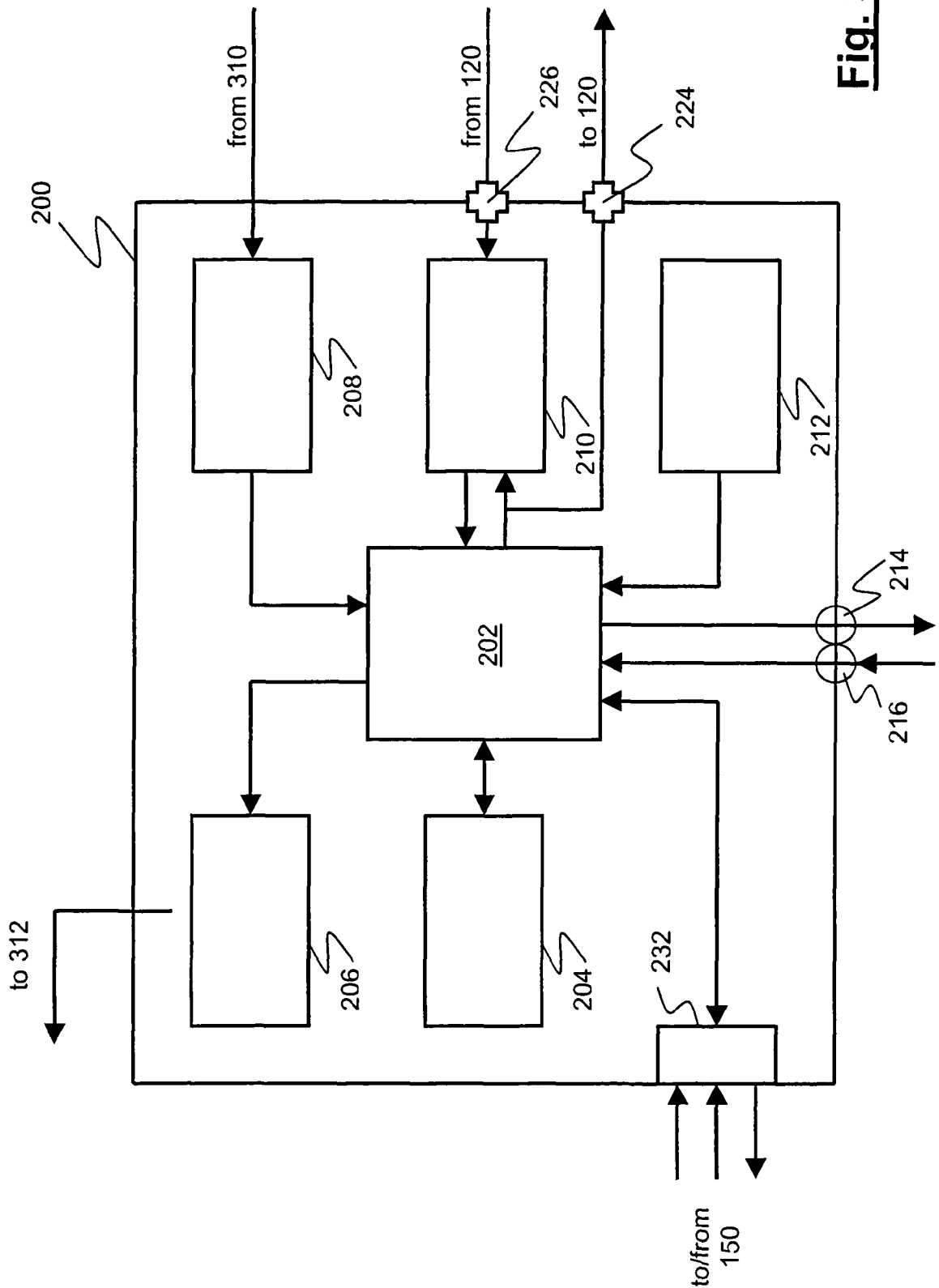
FIG. 3 is a diagram of the eye tracking apparatus shown in FIG. 2.

The eye tracking apparatus 200 as schematically shown in FIG. 3 comprises a microprocessor 202, a memory 204 in particular for storing a shot file representing a desired treatment of a patient's eye, protocoling means 206, detector means 208 for processing video data from the infrared camera 310 to provide position data of the eye or the pupil. The eye tracking apparatus further comprises a comparator means 210 for comparing target position data received from the microprocessor 202 with actual position data received from the scanning apparatus 120. The comparator means provide position data to the scanning apparatus 120 for adjusting the movable mirror to the desired position.

The eye tracking apparatus further comprises a timer 212 being connected to the microprocessor 202 for controlling the processing of the system.

The eye tracking module comprises said first and second interface 224 and 226 for data communication with the scanning apparatus 120. It further comprises said first and second optical interfaces 214 and 216 for data communication with the excimer laser apparatus. In addition it comprises a CAN-controller 232 for data communication to and from the personal computer 150. In addition, the eye tracking apparatus provides a control signal for operating the infrared-light source 312.

When starting the excimer laser eye surgery system in principle the following steps are performed. At the beginning the eye tracking apparatus is provided with the desired treatment shot file from the personal computer via the CAN-controller 232. This treatment shot file is stored in the memory 204. Before starting the treatment a physician will decide when the eye tracking apparatus is switched on. Thereafter any movement of the patient's eye is detected by processing video data from the infrared camera and determining the actual position of the eye or the pupil. The actual position data of the eye is provided from the detector 208 to the microprocessor 202. The microprocessor combines the position data provided from the treatment shot file for a specific shot to be fired and the actual position data of the eye or the pupil and generates target position data. The target position data are provided from the microprocessor via the first interface 224 to the scanning apparatus. The target position data are also provided to the comparator means 210 which further receive said actual position feedback data from the scanning apparatus via the second interface 226. As soon as the comparator means 210 decide that the target position data is equal to the actual position data of the scanning apparatus the comparator means 210 provides a signal to the microprocessor 202 where upon the microprocessor 202 sends a command signal via the first optical interface 214 through the energy monitoring means to the excimer laser apparatus. Using the timing signals provided by the timer 212 the microprocessor 202 monitors whether a feedback signal is received from the excimer laser apparatus via the second optical interface 216. Protocoling means 206 are connected to the microprocessor 202 for storing status information for the individual steps which are performed trough the control of the eye tracking apparatus.

The eye tracking apparatus of the present invention provides the advantage that data can be processed in a fast manner allowing a fast and reliable control of the scanning apparatus and the excimer laser apparatus.

Furthermore, the protocoling means allows for storing protocol information with respect to the operation of the eye tracking apparatus, the scanning apparatus for every shot to be fired wherein the protocol information comprises one or several of the following data, the actual position data of the patient's eye, the actual position data of the scanning apparatus the target position data and any malfunction data.

Figure 4:
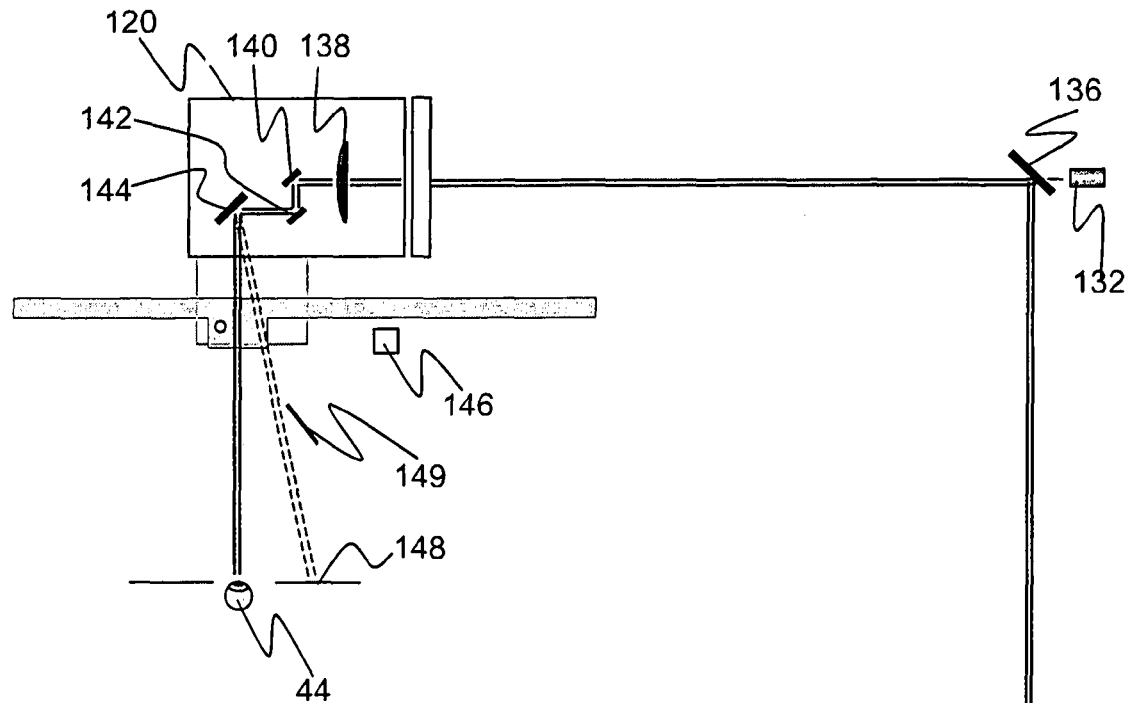
FIG. 4 is a diagram illustrating optical path in the preferred embodiment of an excimer laser eye surgery system according to the present invention.
Figure 4:
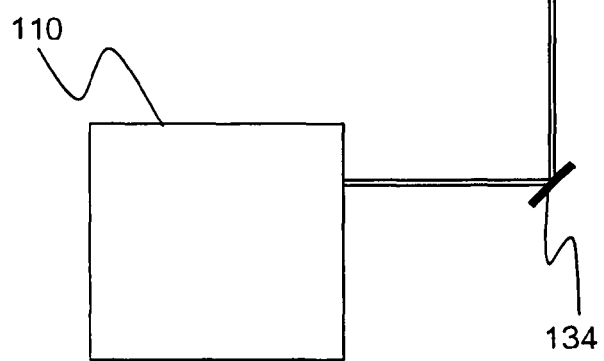

FIG. 4 shows a diagram of an excimer laser eye surgery system in particular the optical path of the pulsed beam from an excimer laser apparatus 110 via a scanning apparatus 120 to a patient's eye 44. More specifically, the pulsed beam from the excimer laser apparatus is guided via a first and a second mirror 134 and 136 to the scanner block 120. The second mirror 136 is a half mirror and allows that the laser beam of an aiming laser 132 is coaligned with a pulsed beam. The pulsed beam is guided through a lens 138 then reflected by a first movable mirror 140, a second movable mirror 142 and a third fixed mirror 144. The first movable mirror is movable in one direction whereas the second movable mirror 142 is moveable in another direction which is preferably orthogonal to the first direction. This allows to direct the pulsed beam to any desired position on the patient's eye 44. On the other hand, the third fixed mirror 144 can be realised as a half-mirror through which a physician may observe the progress during ablation of the surface of the eye through a microscope (not shown). The use of two small movable mirrors has the advantage that smaller mirrors have a lower weight therefore can be brought into position in a very short time.

The two movable mirrors are preferably provided with integrated galvanometers for positioning the mirrors and for providing the actual position. This allows a closed loop scanning as described above with reference to FIGS. 2 and 3.

FIG. 4 further shows a microphone 146 which is arranged at a distance from the treatment surface where the patient's eye is positioned. FIG. 4 further shows a reference surface 148 next to the patient's eye 44 to which the pulsed laser may be directed. The microphone 146 and the reference surface 148 is used for monitoring the pulse energy of the pulsed beam. Before starting a treatment a series of laser pulses will be directed to the reference surfaces 148 which is preferably a PMMA plate. The microphone 146 provides a voltage signal to the energy monitoring means 320. The energy monitoring means compares the received voltage signal with a reference voltage previously measured during a calibration mode. The energy monitoring means compares the actual voltage signal with the reference voltage signal and provides a measure for the laser energy of the laser pulse. The system shown in FIG. 4 further comprises shutter means 149 for providing every n-th laser pulse from a series of laser pulses to the reference surface 148. This has the advantage that the energy monitoring means will process only every n-th laser pulse so that simple processing means can be used.

The signal of the microphone can be additionally used for determining the distance between the treatment surface and the microphone 146. This is achieved by proving the command signal from the eye tracking apparatus not only to the excimer laser apparatus but also to the energy monitoring 320. A command signal triggers a timer inside the energy monitoring means which measures the time until when the microphone 146 receives the noise resulting from hitting the laser pulse onto the reference surface 148. The corresponding time delay can be used for determining the distance.

Figure 5:
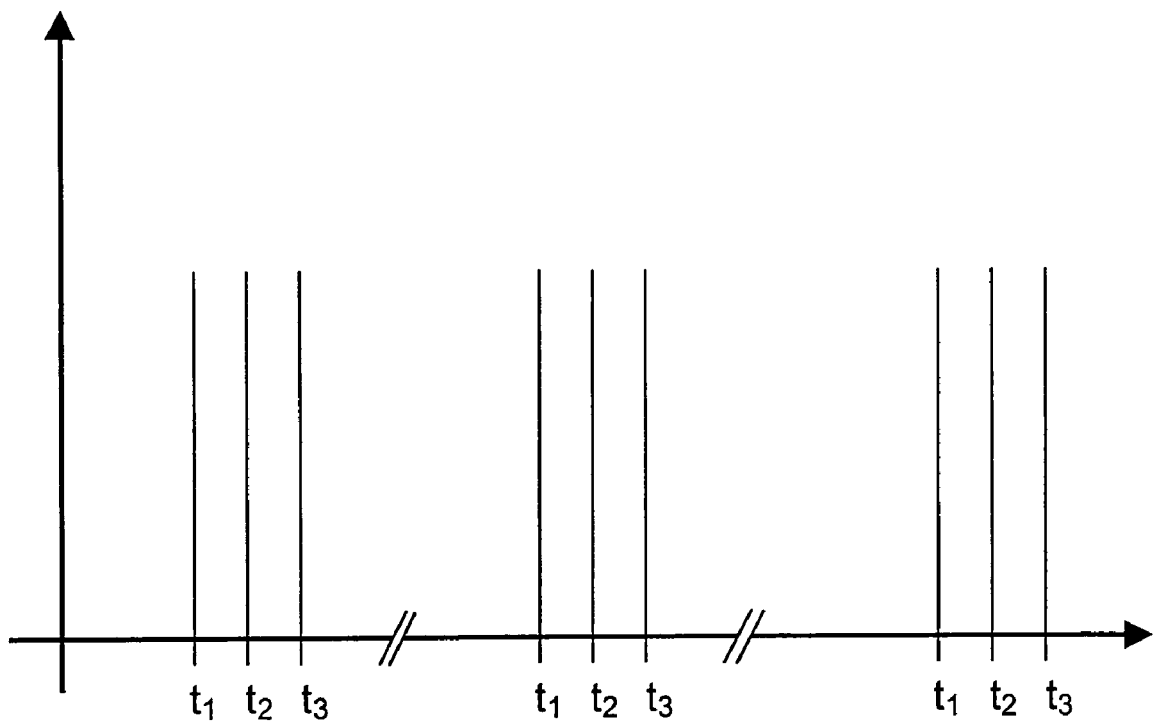
FIG. 5 is a diagram illustrating the timing of signals used in an excimer laser eye surgery system according to the present invention.

FIG. 5 shows the timing diagram for a series of shots fired by the excimer laser apparatus.

More specifically, at a time $t_1$ a command signal is sent to the laser apparatus and at a time $t_2$ the feedback signal is received from the laser apparatus. The time $t_3$ indicates the time window within which the feedback signal from the laser apparatus needs to be received. In case the feedback signal is received within the predetermined time $t_3$ after the command signal is sent to the laser apparatus at time $t_1$ then the system is working properly. However, if a feedback signal would not be received within the predetermined time $t_3$ after a command signal is sent to the laser apparatus a malfunction has occurred and therefore the system stops further processing of the treatment shot file.

The foregoing disclosure and description of the invention are illustrative and explanatory thereof, and whereas changes in the size, shape, materials, components, circuit elements, wiring connections and contacts, as well as in the details of the illustrated circuitry and construction and method of operation may be made without departing from the scope of the invention.

What is claimed is:

1. A system for the treatment of a patient's eye comprising: a laser apparatus, a scanning apparatus and an eye tracking apparatus for determining the actual position of the patient's eye and for generating alignment data of the patient's eye relative to a reference position of the patient's eye to the laser, said eye tracking apparatus being provided with a desired treatment shot file, said scanning apparatus being connected via a first bidirectional bus to the eye tracking apparatus, said laser apparatus being connected via a second bidirectional bus to the eye tracking apparatus, wherein the eye tracking apparatus adjusts the position data for each shot based on said alignment data of the patient's eye and provides aiming control signals representative of the target position data to the scanning apparatus for said shot via said first bidirectional bus and wherein the eye tracking apparatus comprises a comparator for comparing the target position data with the actual position data provided by the scanning apparatus for the shot to be fired and said eye tracking apparatus is sending a command signal to the laser apparatus via said second bidirectional bus for firing the shot when the target position data is equal to the actual position data of the scanning apparatus for the shot to be fired.

2. The system of claim 1, wherein the laser apparatus is sending a feedback signal to the eye tracking apparatus via said second bidirectional bus, when a shot has been fired and wherein preferably the eye tracking apparatus processes to the next shot when a feedback signal is received and wherein the eye tracking apparatus is sending a shut-down signal to the laser apparatus via said second bidirectional bus if no feedback signal is received within a predetermined time.

3. The system of claim 1 wherein the scanning apparatus comprises at least one movable mirror and detector means for providing detection signals representative of the actual position of the movable mirror for the shot to be fired to the patient's eye to the eye tracking apparatus.

4. The system of any of the foregoing claims, wherein the eye tracking apparatus comprises protocolling means for storing protocol information.

5. The system of claim 1 further comprising a computer system being connected to the eye tracking apparatus and the laser apparatus via a third bidirectional bus, wherein said computer system provides the desired treatment shot file to the eye tracking apparatus.

6. The system of claim 1 further comprising a computer system being connected to the eye tracking apparatus and the laser apparatus via a third bidirectional bus, wherein said computer system provides the desired treatment shot file to the eye tracking apparatus, receives and stores protocaol information from the eye tracking apparatus, and transmits and receives control data to/from the laser apparatus and wherein the third bidirectional bus is a CAN-bus and each of the eye tracking apparatus, the scanning apparatus, the laser apparatus and the computer system comprises a CAN-bus controller.

7. The system of claim 1 wherein the scanning apparatus comprises two moveable mirrors, which are positioned according to the target position data, each one of the two mirrors being movable by a respective actuator and the actual position of each moveable mirror being detected by a respective position sensor and one fixed mirror wherein preferably the two moveable mirrors are smaller in size than the fixed mirror.

8. The system of claim 1 further comprising energy monitoring means for monitoring the energy of the laser.

9. The system of claim 8, wherein the energy monitoring means comprises an acoustical sensor for detecting the noise being generated when a laser pulse of the laser apparatus hits on a reference surface.

10. The system of claim 9, wherein said reference surface is a plate made of plastics.

11. The system of claim 8 wherein said acoustical sensor comprises a microphone, which provides a voltage signal, when a laser pulse hits on the reference surface, and a processing means which receives said voltage signal and generates a reference data which is a measure of the laser energy of the laser pulse.

12. The system of claim 11, wherein the laser apparatus comprises an energy control means, which receives the reference data and adjusts the energy of the laser in response to the reference data.

13. The system of claim 9 further comprising shutter means for providing every n-th laser pulse from a series of laser pulses to the reference surface, wherein n is a natural number greater than two, preferably 25.

14. The system of claim 9 wherein the acoustical sensor measures the propagation time of the noise produced at the reference surface, which is used for monitoring the distance between the reference surface and the acoustical sensor.

15. A method for the treatment of a patient's eye using: a laser apparatus having a laser, a scanning apparatus and an eye tracking apparatus, said eye tracking apparatus being provided with a desired treatment shot file, comprising the steps of: determining the actual position of the patient's eye and generating alignment data of the patient's eye relative to a reference position of the patient's eye, adjusting the position data for each shot based on said alignment data of the patient's eye and providing aiming control signals representative of the target position data from the eye tracking apparatus to the scanning apparatus for said shot via a first bidirectional bus and comparing the target position data with the actual position data provided the scanning apparatus for the shot to be fired and sending a command signal from the eye tracking apparatus to the laser apparatus via a second bidirectional bus for firing the shot when the target position data is equal to the actual position of the scanning apparatus for the shot to be fired.

16. The method of claim 15, wherein a feedback signal is send from the laser apparatus to the eye tracking apparatus via said second bidirectional bus, when, a shot has been fired and wherein preferably the next shot is processed by the eye tracking apparatus when a feedback signal is received via said second bidirectional bus and wherein the laser apparatus is shut down if no feedback signal is received within a predetermined time.

17. The method of claim 15 wherein detection signals representative of the actual position of the scanning means for the shot to be fired to the patient's eye are provided from detector means to the eye tracking apparatus.

18. The method of claim 15 further comprising storing protocol information with respect to the operation of the eye tracking apparatus, the scanning means and the laser apparatus for every shot, wherein said protocol information comprises at least one of the following actual position data of the patient's eye, the actual position data of the scanning apparatus, target position data and any malfunction data in protocolling means of the eye tracking apparatus.

19. The method of claim 18 further comprising providing the desired treatment shot file from a computer system to the eye tracking apparatus via a third bidirectional bus, and still further comprising said computer receiving and storing protocol information with respect to the operation of the eye tracking apparatus, and yet further comprising said computer system transmitting and receiving control data to/from the laser apparatus.

20. The method of claim 19 wherein the third bidirectional bus is a CAN-bus and each of the eye tracking apparatus, the scanning apparatus, the laser apparatus and the computer system comprises a CAN-bus controller.

21. The method of claim 20 wherein the scanning apparatus comprises two moveable mirrors, and one fixed mirror wherein the two moveable mirrors are smaller in size than the fixed mirror comprising positioning each one of the two movable mirrors according to the aiming control signals, and detecting the actual position of each moveable mirror.

22. The method of claim 2 further comprising monitoring status data, said status data comprising the energy of the laser apparatus or the position of the laser apparatus with respect to a reference point.

23. The method of claim 22, wherein monitoring comprises the step of detecting the noise being generated when a laser pulse of the laser apparatus hits on a reference surface.

24. The method of claim 23, wherein said reference surface is a plate made of plastics.

25. The method of claim 23 wherein said step of detecting the noise further comprises providing a voltage signal, when a laser pulse hits on the reference surface, processing the voltage signal and generating a reference data which is a measure of the laser energy of the laser pulse.

26. The method of claim 25, further comprising adjusting the energy of the laser apparatus in response to the reference data.

27. The method of claim 22 further providing every n-th laser pulse from a series of laser pulses to the reference surface, wherein n is a natural number greater than two, preferably 25.

28. The method of claim 27 further comprising measuring a propagation time of the noise produced at the reference surface for monitoring the distance between the reference surface and an acoustical sensor.

29. The system of claim 4 the protocol information comprises at least one of the following: actual position data of the patient's eye, the actual position data of the scanning apparatus, target position data, and malfunction data.

30. The system of any of claim 5 wherein the third bidirectional bus is a CAN-bus and the eye tracking apparatus comprises a CAN-bus controller.

31. The system of claim 1 further comprising a computer system being connected to the eye tracking apparatus and the laser apparatus via a third bidirectional bus, wherein said computer system receives and stores protocol information from the eye tracking apparatus.

32. The system of claim 31 wherein the third bidirectional bus is a CAN-bus and the eye tracking apparatus comprises a CAN-bus controller.

33. The system of claim 1 further comprising a computer system being connected to the eye tracking apparatus and the laser apparatus via a third bidirectional bus, wherein said computer system transmits and receives control data to/from the laser apparatus.

34. The system of any of claim 33 wherein the third bidirectional bus is a CAN-bus and each of the scanning apparatus, the laser apparatus and the computer system comprises a CAN-bus controller.

35. The method of claim 24 wherein said step of detecting the noise further comprises providing a voltage signal, when a laser pulse hits on the reference surface, processing the voltage signal and generating a reference data which is a measure of the laser energy of the laser pulse.

36. The method of claim 35, further comprising adjusting the energy of the laser apparatus in response to the reference data.

* * * * *